United States Patent [19]

Cassinelli et al.

[11] 4,183,919
[45] Jan. 15, 1980

[54] ANTITUMOR GLYCOSIDES, PROCESS FOR THEIR PREPARATION INCLUDING INTERMEDIATES THEREFOR AND THEIR USE

[75] Inventors: Giuseppe Cassinelli, Voghera; Federico Arcamone, Nerviano; Aurelio Di Marco, Milan, all of Italy

[73] Assignee: Farmitalia Carlo Erba S.p.A., Milan, Italy

[21] Appl. No.: 860,447

[22] Filed: Dec. 14, 1977

[30] Foreign Application Priority Data

Dec. 22, 1976 [GB] United Kingdom ............... 53454/76

[51] Int. Cl.² .............................................. A61K 31/70
[52] U.S. Cl. ........................................ 424/180; 536/4; 536/17 A
[58] Field of Search ..................... 536/4 A, 17 A, 4; 424/180

[56] References Cited

U.S. PATENT DOCUMENTS

| | | | |
|---|---|---|---|
| 3,976,667 | 8/1976 | Kelly | 260/365 |
| 4,067,969 | 1/1978 | Penco et al. | 424/180 |

OTHER PUBLICATIONS

Di Marco et al., Journ. Med. Chem., vol. 17, No. 3, pp. 335–337, (1974).

*Primary Examiner*—Ethel G. Love
*Attorney, Agent, or Firm*—Hubbell, Cohen, Stiefel & Gross

[57] ABSTRACT

Disclosed is a new class of antitumor glycoside antibiotics of the formula (IA):

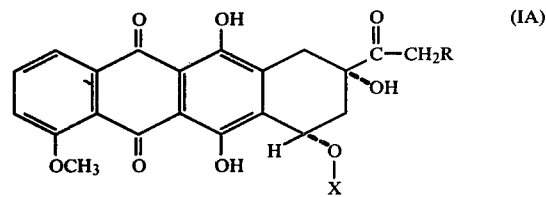

wherein R is hydrogen or hydroxy; and X is

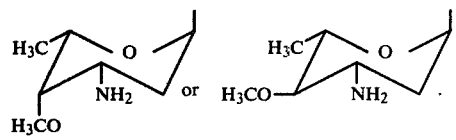

These compounds are prepared, using novel intermediates, by condensing the appropriate aglycone and amino-deoxy sugar to form the α-glycosidic linkage.

8 Claims, No Drawings

ANTITUMOR GLYCOSIDES, PROCESS FOR THEIR PREPARATION INCLUDING INTERMEDIATES THEREFOR AND THEIR USE

CROSS REFERENCE TO RELATED APPLICATIONS

This application is related to, and incorporates by reference the contents of application Ser. No. 675,696, filed Apr. 9, 1976 now U.S. Pat. No. 4,112,076, U.S. Pat. No. 3,803,124 and U.S. Pat. No. 4,039,663, all of which are owned by the unrecorded assignee hereof.

BACKGROUND OF THE INVENTION

1. Field of the Invention

The present invention relates to antitumor glycosides of the anthracycline type, in particular, certain 4'-O-methyldaunomycin (and adriamycin) derivatives, their preparation, intermediates therefor and their use in antitumor therapy.

2. The Prior Art

The present compounds which are derivatives of daunomycin and adriamycin, both of which are known antitumor antibiotics, are prepared from the aglycone of daunomycin, i.e., daunomycinone, a known compound.

SUMMARY OF THE INVENTION

The invention provides, in one aspect thereof, a new class of antitumor antibiotics of the formula (IA):

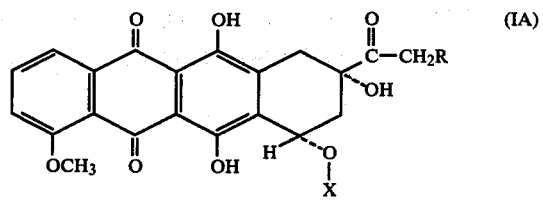

wherein R is hydrogen or hydroxy; and X is

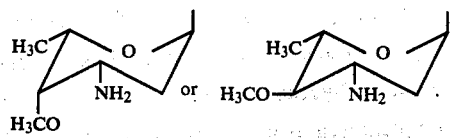

Clearly, when R is hydrogen, these compounds are daunomycin derivatives and when R is hydroxy they are adriamycin derivatives. These new antitumor compounds are: 4'-O-methyl-daunomycin, 4'-O-methyl-adriamycin, 4'-epi-4'-O-methyl-daunomycin and 4'-epi-4'-O-methyl-adriamycin.

The process for making these compounds also comprises part of the invention. According to the process of the invention, a tetracylic aglycone having a hydroxyanthraquinone chromophoric system of the formula I:

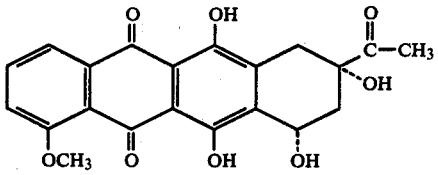

is glycosidically linked to a 3-amino-2,3,6-trideoxy-4-O-methyl-L-hexopyranose.

In performing the process, the aglycone of the formula I, which is daunomycinone, is condensed with a protected (N-trifluoroacetyl) 1-halo derivative of an amino-deoxy sugar selected from the group consisting of 2,3,6-trideoxy-3-trifluoroacetamido-4-O-methyl-L-lyxo-hexopyranosyl chloride (II-E), and 2,3,6-trideoxy-3-trifluoroacetamido-4-O-methyl-L-arabino-hexopyranosyl chloride (III-E),

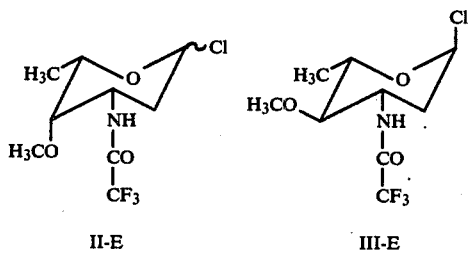

to give respectively, the protected α-glycosides of the formulae IV and VI:

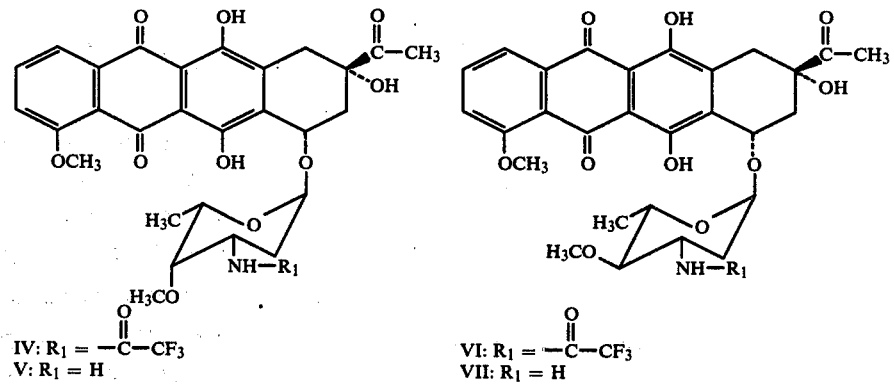

from which, after removal of the N-trifluoroacetyl protecting group, the final products V and VII are obtained.

The condensation reaction between the aglycone (I) and the protected halo sugar (II-E or III-E) to form the α-glycosidic linkage is carried out in an inert solvent, such as chloroform or methylene dichloride in the presence of a soluble silver salt catalyst, such as silver trifluoromethanesulphonate (AgSO₃CF₃) and a molecular sieve as a dehydrating agent in accordance with the method described in application Ser. No. 675,696, filed Apr. 9, 1976.

The protected halo sugars II-E and III-E are also novel compounds and are thus within the scope of the present invention.

The starting materials for the preparation of halo sugars II-E and III-E are, respectively: methyl 2,3,6-trideoxy-3-trifluoroacetamido-α-L-lyxo-hexopyranoside (II-A) and methyl 2,3,6-trideoxy-3-trifluoroacetamido-α-L-arabino-hexopyranoside (III-A), both of which are described in U.S. Pat. No. 4,039,663.

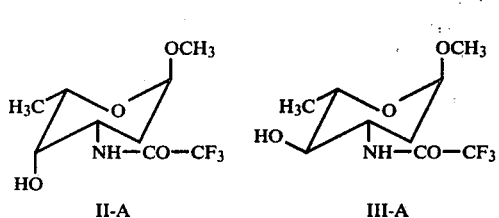

Treatment of the starting materials (II-A and III-A) with diazomethane-borontrifluoride etherate reagent in methylene dichloride (as described by J. O. Deferrari et al, in Methods in Carbohydrate Chemistry, Vol. VI, p. 365, 1972, Academic Pres., New York and London) gives the corresponding previously unknown 4-O-methyl derivatives (II-B and III-B) in good yield.

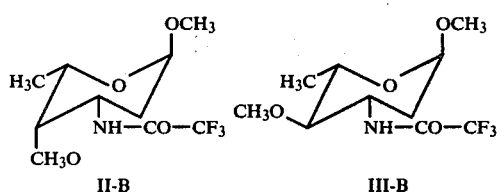

Acid hydrolysis of compounds II-B and III-B, respectively, affords the corresponding compounds II-C and III-C containing a free hydroxyl group in position 1.

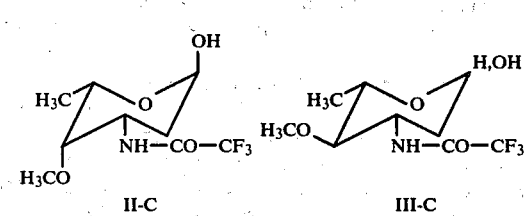

Compounds II-C and III-C, respectively, are reacted with p-nitrobenzoyl chloride in pyridine in order to obtain the corresponding 1-O-p-nitrobenzoyl derivatives II-D and III-D

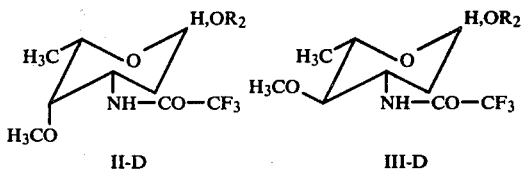

wherein $R_2$ is

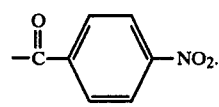

Finally, compounds II-D and III-D are subjected to treatment with dry hydrogen chloride in anhydrous methylene dichloride to give the corresponding 1-chloro derivatives (II-E and III-E).

In order to prepare the compounds of formula (IA), i.e., those wherein R is hydrogen or hydroxy, and X is

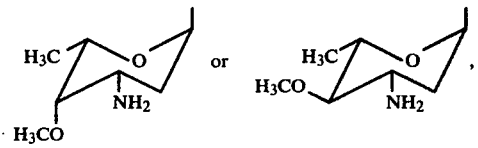

the above-mentioned condensation reaction is effected by using daunomycinone (I) as the aglycone and 2,3,6-trideoxy-4-O-methyl-3-trifluoroacetamido-L-lyxo-hexopyranosyl chloride (II-E) or 2,3,6-trideoxy-4-O-methyl-3-trifluoroacetamido-α-L-arabinohexopyranosyl chloride (III-E) as the protected halo sugar reagent. The coupling reaction affords the protected α-glycosides IV and VI from which, by mild alkaline treatment in order to remove the N-trifluoroacetyl group, 4'-O-methyl-daunomycin (V) and 4'-epi-4'-O-methyl-daunomycin (VII), respectively, are obtained and isolated as the crystalline hydrochlorides.

Subsequent treatment of compounds (V) and (VII) in accordance with the methods described in U.S. Pat. No. 3,803,124, leads respectively, to 4'-O-methyladriamycin (VIII) and 4'-epi-4'-O-methyl-adriamycin (IX).

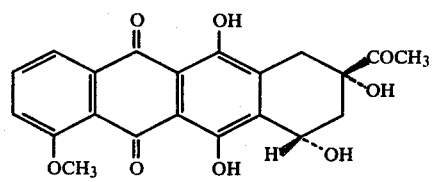

I

+III-E

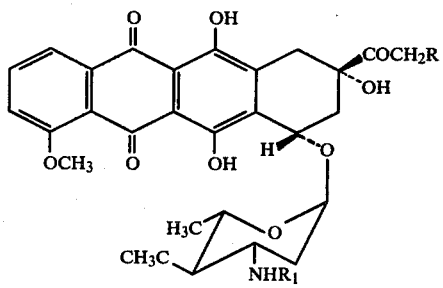

VI: R = H, R₁ = COCF₃
VII: R = R₁ = H
IX: R = OH, R₁ = H

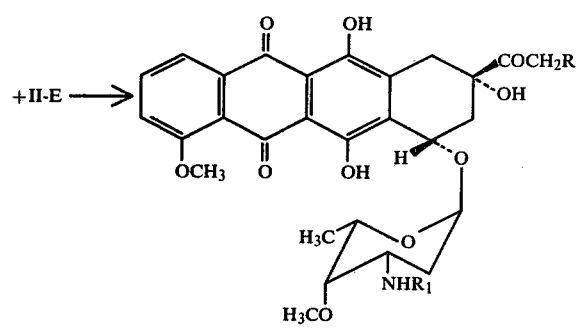

IV: R = H, R₁ = COCF₃
V: R = R₁ = H
VIII: R = OH, R₁ = H

DESCRIPTION OF THE PREFERRED EMBODIMENTS

The invention will now be described in greater detail in conjunction with the following examples (wherein all parts given are by weight unless otherwise specified) and biological data.

EXAMPLE 1

Preparation of the intermediate 2,3,6-trideoxy-4-O-methyl-3-trifluoroacetamido-L-lyxo-hexopyranosyl chloride (II-E)

A solution of 2.57 g.; 10 mmoles of methyl 2,3,6-trideoxy-3-trifluoroacetamido-α-L-lyxo-hexopyranoside (II-A) in 45 ml. of dry methylene dichloride was treated at 0° C. with 0.1 ml. of boron trifluoride etherate. While maintaining the temperature at 0°, an excess of diazomethane dissolved in methylene dichloride was added until a faint yellow color persisted. After 90 minutes at 0°, a white solid (polymethylene) was removed by filtration, and the filtrate was washed successively with 10% sodium bicarbonate solution and with water, after which it was dried with anhydrous magnesium sulfate. The residue which was obtained by evaporation was crystallized from ethyl ether-hexane to give pure methyl 2,3,6-trideoxy-3-trifluoroacetamido-4-O-methyl-α-L-lyxo-hexopyranoside (II-B, 2.3 g., 85%): m.p. 137°–138°; [α]$_D$= −150° (c=1, in CHCl₃); mass spectrum m/e 271 (M⁺). The pmr spectrum (CDCl₃) showed absorptions at 1.23 (d, CH₃—C—5), 3.23 and 3.40 (two s, —OCH₃) and 4.70δ (broad s, C—1—H).

A solution of 2.17 g.; 8 mmoles of compound II-B in 40 ml. of acetic acid was added to 160 ml. of water and heated at 100° for 1 hour. The solution was evaporated to form a residue, from which, upon crystallization from acetone-hexane gave 2,3,6-trideoxy-3-trifluoroacetamido-4-O-methyl-α-L-lyxo-hexopyranose (II-C; 2 g.; 97%): m.p. 193°–194°; [α]$_D$= −130° (c=0.97, n CHCl₃); mass spectrum m/e 257 (M⁺). The pmr spectrum (CDCl₃) showed absorptions at: 1.23 (d, CH₃—C—5), 3.50 (s, CH₃O) and 5.40δ (broad s, C—1—H).

A solution of 1.68 g.; 6.53 mmoles of compound II-C in 48 ml. of dry pyridine was treated at 0° with 2.52 g. of p-nitrobenzoyl chloride under stirring. After 14 hours at room temperature the reaction mixture was poured into ice-water and the resulting precipitate was filtered off and washed with water to neutrality. The precipitated 1-p-nitrobenzoate (mixture of α and β anomers) was dissolved in chloroform and dried over magnesium sulfate. The residue obtained by evaporation of the chloroform gave 2.4 g. of 2,3,6-trideoxy-4-O-methyl-1-O-p-nitrobenzoyl-3-trifluoroacetamido-L-lyxo-hexopyranose (II-D, 92%): m.p. 168°–170°; [α]$_D$= −39° (c=0.45, in CHCl₃) mass spectrum m/e=240

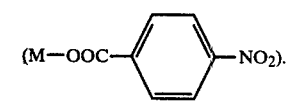

A solution of 1.05 g.; 2.5 mmoles of compound II-D in dry methylene dichloride was saturated at 0° with anhydrous hydrogen chloride. The resulting precipitate of p-nitrobenzoic acid was filtered off under anhydrous conditions and the filtrate was evaporated to a residue which was 2,3,6-trideoxy-4-O-methyl-3-trifluoroacetamido-L-lyxo-hexopyranosyl chloride (II-E, 0.69 g.). This compound was suitable for use in the coupling reaction without further purification.

EXAMPLE 2

Preparation of the intermediate 2,3,6-trideoxy-4-O-methyl-3-trifluoroacetamido-α-L-arabino-hexopyranosyl chloride (III-E)

Treatment of 2.57 g; 10 mmoles of methyl 2,3,6-trideoxy-3-trifluoroacetamido-α-L-arabino-hexopyranoside (III-A) in methylene dichloride with diazomethane/boron-trifluoride, as described in Example I gave the corresponding 4-O-methylderivative (III-B, 1.7 g., 63%): m.p. 185°; $[\alpha]_D^{23°} = -101°$ (c=1, in CHCl$_3$); mass spectrum m/e 271 (H+); pmr spectrum (CDCl$_3$); 1.31 (d, CH$_3$—C—5), 3.30 and 3.43 (two s, OCH$_3$) and 4.70δ (broad s, C—1—H). Acid hydrolysis of compound III-B as in Example I (1.63 g., 6 mmoles) gave 2,3,6-trideoxy-4-O-methyl-3-trifluoroacetamido-L-arabino-hexopyranose (III-C, 1.51 g., 98%): m.p. 201°; $[\alpha]_D^{23°} = -12.7°$ (c=0.48, in CHCl$_3$); mass spectrum m/e 257 (M+).

Treatment of compound III-C (1.41 g., 5.5 mmoles) with p-nitrobenzoyl chloride in pyridine as described in Example I gave the corresponding 1-O-p-nitrobenzoyl derivative (III-D, 1.78 g., 80%): m.p. 159°–160°; $[\alpha]_D^{23°} = -33.5°$ (c=0.47, in CHCl$_3$); mass spectrum m/e=

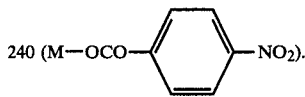

240 (M—OCO—⟨ ⟩—NO$_2$).

A solution of compound III-D (1.6 g., 4 mmoles) in dry methylene dichloride was saturated at 0° with anhydrous hydrogen chloride. After filtration of the precipitated p-nitrobenzoic acid, the solution was evaporated to dryness to give the resulting 2,3,6-trideoxy-4-O-methyl-3-trifluoroacetamido-α-L-arabino-hexopyranosyl chloride (III-E, 1.1 g.); pmr spectrum (CDCl$_3$): 1.34 (d, CH$_3$—C—S), 3.44 (s, CH$_3$O—C—H), and 6.17δ (br s, C—1—H).

EXAMPLE 3

4'-O-Methyl-daunomycin (V)

To a solution of 1 g.; 2.5 mmoles of daunomycinone in 100 ml. of dry methylene dichloride there were added 0.69 g. of 2,3,6-trideoxy-4-O-methyl-3-trifluoroacetamido-L-lyxo-hexopyranosyl chloride (II-E) and 7 g. of molecular sieve (4 A Merck), which was then treated with 0.78 g. of AgSO$_3$CF$_3$ in anhydrous ethylether under vigorous stirring. After 2 hours at room temperature, the reaction mixture was neutralized with a saturated aqueous solution of NaHCO$_3$, and the organic phase was separated and evaporated under vacuum. Chromatographic purification of the crude residue on a column of silicic acid, using 99:1 chloroform:acetone as the eluent, gave 0.9 g. of 4'-O-methyl-N-trifluoroacetyldaunomycin (IV): m.p. 151°–152°; $[\alpha]_D = +250°$ (c=0.06, in CHCl$_3$). The p.m.r. spectrum (CDCl$_3$) showed absorption at 1.33 (d, CH$_3$—C—5'), 2.40 (s, CH$_3$—CO), 3.53 (s, C—4'—O—CH$_3$), 4.03 (s, C—4—O—CH$_3$), 5.20 (broad s, C—7—H), 5.50 (broad s, C—1'—H), 6.43 (NH), 7.16–8.06 (m, aromatic protons), 16.26 and 17.74δ (two s, phenolic OH).

A solution of 0.5 g. of compound IV in 30 ml. of acetone was treated with 30 ml. of 0.1 N aqueous sodium hydroxide and stirred under nitrogen at room temperature. After 1 hour the reaction mixture was adjusted to pH 3.5 with 1 N aqueous hydrogen chloride and then extracted with chloroform to eliminate impurities. The aqueous phase, adjusted to pH 8.5, was extracted twice with chloroform (50 and 30 ml. portions). The combined organic extracts were dried over Na$_2$SO$_4$, concentrated to a small volume and acidified to pH 4.5 with 0.5 N methanolic hydrogen chloride. Addition of excess diethyl ether gave 4'-O-methyldaunomycin (V) as the hydrochloride (0.4 g., 90%): m.p. 173° (dec.); $[\alpha]_D = +210°$ (c=0.04, in CH$_3$OH); TLC on Merck Kieselgel F$_{254}$ plate using 150:42:6 chloroform-methanol-water as solvent; Rf 0.40 (daunomycin Rf 0.25).

EXAMPLE 4

4'-O-Methyl-adriamycin (VIII)

0.35 g. of 4'-O-methyl-daunomycin hydrochloride (V) dissolved in a mixture of 5 ml. of anhydrous methanol, 14 ml. of dioxane and 0.35 ml. of ethyl orthoformate was treated with 1.4 ml. of a solution of 0.93 g. of bromine in 10 ml. of chloroform. After 3 hours at 10° C. the reaction mixture was poured into a mixture of 70 ml. of ethyl ether and 35 ml. of petroleum ether. The resulting red precipitate, after being filtered and washed with ethyl ether several times to completely remove the acidity was dissolved in a mixture of 10 ml. of acetone and 10 ml. of 0.25 N aqueous hydrogen bromide. After 15 hours at room temperature, 6 ml. of water were added to the mixture and the solution was extracted several times with chloroform to remove the aglycones. Thus, the aqueous phase was extracted with n-butanol until the extracts became colorless. Evaporation of the combined organic solvent extracts (n-butanol) under vacuum to a small volume (about 6 ml.) and precipitation with ethyl ether yielded 0.30 g. of the 14-bromo derivative. This latter compound was dissolved in 7 ml. of 0.25 N aqueous hydrogen bromide and treated with 0.5 g. of sodium formate in 5 ml. of water. The reaction mixture was kept at room temperature with stirring for 48 hours, and then, 1 N hydrochloric acid was added until the pH reached 4. The resulting mixture was extracted with a 1:1 mixture of ethyl ether and ethyl acetate in order to remove some lipophilic impurities. The aqueous phase, after being adjusted to pH 7.6 with aqueous NaHCO$_3$ was repeatedly extracted with chloroform until the extracts were colorless. The combined chloroform extracts were dried with Na$_2$SO$_4$ and evaporated to a small volume (about 30 ml.) under vacuum. The resulting red solution, adjusted to pH 3.5 with anhydrous methanolic hydrogen chloride, was added with excess ethyl ether to give 0.20 g. of 4'-O-methyl-adriamycin (VIII), as the hydrochloride: m.p. 177° (dec.); $[\alpha]_D^{23°} + 259°$ (c=0.046, in CH$_3$OH).

EXAMPLE 5

4'-Epi-4'-O-methyl-daunomycin (VII)

The synthesis of the compound VII, starting from daunomycin-one (I) and 2,3,6-trideoxy-4-O-methyl-3-trifluoroacetamido-α-L-arabino-hexopyranosyl chloride (III-E) was performed according to the procedure described in Example III.

4'-Epi-4'-O-methyldaunomycin (VII) was obtained as the hydrochloride in the form of orange-red crystals: m.p. 192° (dec.); $[\alpha]_D^{23°} = +270°$ (c=0.047, in $CH_3OH$).

EXAMPLE 6

4'-Epi-4'-O-methyl-adriamycin (IX)

The 14-bromo-derivative of compound VII was obtained and successively hydroxylated at the 14-position according to the procedure described in Example 4. By this procedure, 4'-epi-4'-O-methyl-adriamycin (IX) was obtained as the hydrochloride in the form of orange-red crystals: m.p. 170° (dec.); $[\alpha]_D^{23°} = +252°$ (c=0.052, in $CH_3OH$).

Biological Activity

The new antitumor compounds of the invention are useful therapeutic agents for treating certain mammalian tumors.

Compounds of formula IA according to the invention were tested in $BDF_1$ mice $(C57BL/6 \times DBA)_1$, injected i.p. with $10^5$ cells/mouse of $L_{1210}$ ascitic leukemia, and $10^6$ cells/mouse of $P_{388}$ ascitic leukemia. Treatment with the instant compound was performed i.p. on day 1 after tumor inoculation. The compounds were dissolved in distilled water as the hydrochlorides. Daunomycin and daunomycin derivatives were tested against $P_{388}$ leukemia, which is very sensitive to the anthracyclines antitumor activity. The data reported in Table 1 show that 4'O-methyldaunomycin at a dose of 4.4 mg./kg. is more active than daunomycin; 4'-epi-4'-O-methyl-daunomycin displaced a wide range of active doses (from 4.4 to 20 mg./kg.) and is less toxic than daunomycin. At the optimal non-toxic doses, daunomycin (2.9 mg./kg.) and 4'-epi-4'-O-methyldaunomycin (20 mg./kg.) showed the same antitumor activity.

The corresponding derivatives of adriamycin were tested against $L_{1210}$ leukemia, because $P_{388}$ leukemia is too sensitive to adriamycin and it is therefore very difficult to assess the superiority of new compounds.

The data reported in Table 2 show that, in two separate experiments, 4'-O-methyladriamycin is more active than adriamycin: at doses of 4.4 and 6.6 mg./kg., this compound caused an increase in the life span of the test animals of from 130 to 212%, while adriamycin at the optimal (non toxic) dose of 6.6 mg./kg. caused an increase in the life span of 75%.

This higher activity of 4'-O-methyladriamycin, in comparison with adriamycin, against $L_{1210}$ leukemia, is of great relevance. 4'-epi-4'-O-methyladriamycin showed an antitumor activity of the same order of magnitude of adriamycin, and a reduced toxicity.

In summary, the results presented below show that the substitution of the hydroxyl group at the 4'-position of the aminosugar, by a methoxy group, brings about an increase in the antitumor activity which is dramatic in the case of adriamycin; epimerization of the 4' substituent causes a decrease of the general toxicity, as assessed in tumor bearing mice.

TABLE 1

| Activity Against $P_{388}$ Leukemia | | | |
|---|---|---|---|
| Compound | Dose (mg./kg.) | T/C[1] % | No. of toxic deaths/total |
| Daunomycin | 2.9 | 169 | |
|  | 4.4 | 169 | 2/10 |
|  | 6.6 | 160 | 7/10 |
| 4'-O-methyldauno-mycin . HCl (V) | 2.9 | 156 | |
|  | 4.4 | 191 | 3/10 |

TABLE 1-continued

| Activity Against $P_{388}$ Leukemia | | | |
|---|---|---|---|
| Compound | Dose (mg./kg.) | T/C[1] % | No. of toxic deaths/total |
|  | 6.6 | 139 | 7/10 |
| 4'-epi-4'-O-methyl-daunomycin . HCl (VII) | 4.4 | 150 | |
|  | 10.0 | 143 | |
|  | 20.0 | 174 | |
|  | 40.0 | 34 | 9/9 |

[1]Median survival time of treated mice, over median survival time of controls. × 100.

TABLE 2

| Activity Against $L_{1210}$ Leukemia | | | | |
|---|---|---|---|---|
|  |  | T/C % | | |
| Compound | Dose (mg./kg.) | 1st Exp. | 2nd Exp. | No. of toxic deaths/total |
| Adriamycin | 4.4 | 169 | | |
|  | 6.6 | 175 | 175 | |
|  | 10.0 | 187 | 187 | 3/20 |
| 4'-O-methyladria-mycin . HCl (VIII) | 4.4 | 287 | 312 | |
|  | 6.6 | 231 | 275 | 1/20 |
|  | 10.0 | 75 | 62 | 17/18 |
| 4'-epi-4'-O-methyl-adriamycin . HCl (IX) | 6.6 | 169 | | |
|  | 10.0 | 187 | | |
|  | 15.0 | 181 | | 2/10 |
|  | 22.5 | 87 | | 9/10 |

Variations and modifications can, of course, be made without departing from the spirit and scope of the invention.

Having thus described our invention, what we desire to secure by Letters Patent and hereby claim is:

1. A compound of the formula:

(IA)

wherein R is hydrogen or hydroxy; and X is and the hydrochlorides thereof.

2. A compound according to claim 1, which is 4'-O-methyl-daunomycin.

3. A compound according to claim 1, which is 4'-O-methyl-adriamycin.

4. A compound according to claim 1, which is 4'-epi-4'-O-methyl-daunomycin.

5. A compound according to claim 1, which is 4'-epi-4'-O-methyl-adriamycin.

6. An N-trifluoroacetyl protected glycoside of the formula:

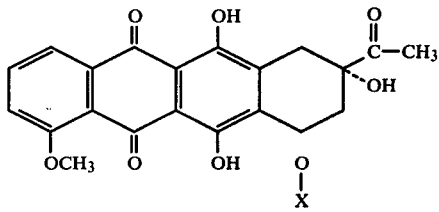

wherein X is

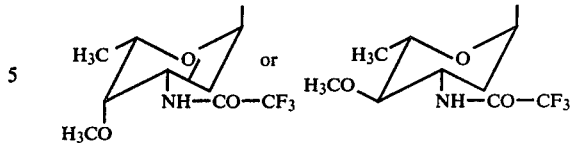

7. A method of inhibiting the growth of $P_{388}$ leukemia and $L_{1210}$ leukemia in a host afflicted therewith, said method comprising intraperitoneally administering to said host a compound according to claim 1 in an amount sufficient to inhibit the growth thereof.

8. A pharmaceutical composition for inhibiting the growth of $P_{388}$ leukemia comprising a compound of claim 1 in an amount sufficient to inhibit the growth thereof.

* * * * *